US006423059B1

(12) United States Patent
Hanson et al.

(10) Patent No.: US 6,423,059 B1
(45) Date of Patent: Jul. 23, 2002

(54) RADIO FREQUENCY ABLATION APPARATUS WITH REMOTELY ARTICULATING AND SELF-LOCKING ELECTRODE WAND

(75) Inventors: David A. Hanson; Raed N. Rizq, both of Minneapolis; Jodi L. Balik, Eden Prairie; Samira Tahvildari, St. Paul; Mandar G. Sukhatankar, Minneapolis; William K. Durfee, Edina; Arthur G. Erdman, New Brighton, all of MN (US)

(73) Assignee: Sulzer Medica USA Inc., Houston, TX (US)

( * ) Notice: Subject to any disclaimer, the term of this patent is extended or adjusted under 35 U.S.C. 154(b) by 0 days.

(21) Appl. No.: 09/441,549

(22) Filed: Nov. 16, 1999

(51) Int. Cl.$^7$ .............................................. A61B 18/18
(52) U.S. Cl. ......................... 606/41; 604/528; 600/585
(58) Field of Search ..................... 606/41, 46; 600/585, 600/131, 146, 147, 148, 149; 604/528

(56) References Cited

U.S. PATENT DOCUMENTS

| | | | |
|---|---|---|---|
| 4,898,577 A | * 2/1990 | Badser et al. ................ | 604/528 |
| 4,911,148 A | * 3/1990 | Sosnowski et al. .......... | 600/146 |
| 4,998,916 A | 3/1991 | Hammerslag et al. ........ | 604/95 |
| 5,395,327 A | * 3/1995 | Lundquist et al. ........... | 600/585 |
| 5,484,407 A | * 1/1996 | Osypka ....................... | 600/585 |
| 5,489,270 A | * 2/1996 | Van Erp ...................... | 604/528 |
| 5,514,130 A | 5/1996 | Baker .......................... | 606/41 |
| 5,681,282 A | 10/1997 | Eggers et al. ................ | 604/114 |
| 5,697,281 A | 12/1997 | Eggers et al. ................ | 604/114 |
| 5,697,909 A | 12/1997 | Eggers et al. ................ | 604/114 |
| 5,716,366 A | 2/1998 | Yates .......................... | 606/139 |
| 5,785,705 A | 7/1998 | Baker .......................... | 606/32 |
| 5,807,393 A | 9/1998 | Williamson, IV et al. .... | 606/32 |
| 6,042,562 A | * 3/2000 | Amor .......................... | 600/585 |

OTHER PUBLICATIONS

Eggers, Philip, et al. "Coblation: A Newly Described Method for Soft Tissue Surgery" Research Outcomes in Arthoscopic Surgery, vol. 2, No. 1, Nov., 1997 (ArthroCare Corp.).

Wolf, Eugene M. "Capsular Shrinkage Technical Guide—Using Arthrocare Caps X Arthrowand", Jun. 1998 (Arthro-Care Corp.).

Stetson, William B. "Time and Cost Savings of Coblation Technology in Subarcromial Decompression" Research Outcomes in Arthroscopic Surgery vol. 3, no. 2, Jan., 1999 (ArthroCare Corp.).

ArthroCare Corporation—the Company, www.arthrocare.com, printed May, 1999.

"Design of Tip Electrodes for Arthroscopic Radiofrequency Devices" Ethicon, Inc., May, 1998 "Mitek Products" Ethicon, Inc, www.mitek.com, printed May, 1999.

Rae–Dupree, Janet "Shrink don't Slice", San Jose Mercury News, Jun. 24, 1997.

"Oratec Interventions, Inc." www.oratec.com, printed May, 1999.

"Orastat Electro Thermal Shaver Coagulator", Oratec Interventions, Inc. Jun. 1998.

"The IDET Technique with the Spine CATH System" Oratec Interventions, Inc. Jan., 1999.

Philippon, Marc J. "Arthroscopic Monopolar Thermal Capsulorrhaphy for Instability of the Hip" Oratec Interventions, Inc., 1998.

* cited by examiner

*Primary Examiner*—Linda C. M. Dvorak
*Assistant Examiner*—David M. Ruddy
(74) *Attorney, Agent, or Firm*—Christopher R. Kirby; Timothy L. Scott; Kenneth S. Barrow

(57) ABSTRACT

A radio frequency ablation apparatus having an application wand which is articulating and self-locking in a selected configuration. The wand has a handle having a thumb wheel apparatus. A threaded bore extends coaxially through the thumb wheel. A threaded tube received in the threaded bore translates a wire which extends to the distal end of the wand. At the distal end of the wand, the wire passes over a bendable section in the wand. Pushing or pulling the wire bends the distal tip through a range of angles on both sides of a neutral linear position. The distal tip remains self-locked in a selected position when the thumb screw is not turned.

45 Claims, 3 Drawing Sheets

RADIO FREQUENCY ABLATION APPARATUS WITH REMOTELY ARTICULATING AND SELF-LOCKING ELECTRODE WAND

BACKGROUND OF THE INVENTION

1. Field of the Invention

This invention relates generally to the field of electrosurgery and more particularly, to radio frequency apparatus and to wands bearing electrodes for delivering such radio frequency therapy.

2. Background of the Invention

Instability of joints is a significant cause of disability or limitation in patients who are active in their daily activities, work or sports. The joints provide varying degrees of freedom of movement. The knee, for instance, is a joint with essentially one degree of freedom, acting primarily as a hinge. A second, subordinate degree of freedom, rotation around the long axis of the leg, only occurs when the knee is flexed. Thus, the knee provides great stability in complete extension when the knee bears the weight of the body, and great mobility when a certain measure of flexion is achieved, as in walking or running. Reduced interlocking of articulating surfaces provide stability coupled with mobility, but render the knee liable to sprains and dislocations. The shoulder is also vulnerable. It is an open ball and socket joint exhibiting three axes and three degrees of freedom, thereby providing great freedom of movement at the expense of stability. The possibility of injury to the shoulder joint is, therefore, quite high.

Joints such as the knee and shoulder are comprised of articulating surfaces at the ends of adjoining bones and coverings of hyaline cartilage surrounded by a soft tissue joint capsule which maintains constant contact with the cartilage surfaces. The joint capsule also maintains the synovial fluid within the joint. Synovial fluid lubricates the joint surfaces. Around the joint capsule, ligaments reinforce and hold the joints together while controlling or restricting certain movements of the joint. Ligaments, joint capsule, and connective tissue are comprised mainly of collagen.

When a joint becomes unstable, its soft tissue or bony structure allows for excessive motion of the joints surfaces relative to each other, and in a direction not normally permitted by the ligaments or capsule. One contributing cause of instability is lengthening of the cartilage comprising ligaments, joint capsule, and connective tissue which surround the joint. The more motion a joint normally provides, the looser the soft tissue and cartilage surrounding the joint. This makes some joints inherently more unstable than others. The shoulder, for example, is a loose joint with great mobility. It is consequently prone to instability.

Instability of the shoulder and other joints can occur congenitally, developmentally or traumatically and often becomes recurrent, requiring surgical repair. Surgical repair often involves tightening the surrounding tissues which have become too loose to constrain the motion of the joint. These procedures have been performed through open surgical techniques, often requiring hospitalization and prolonged rehabilitation.

More recently, endoscopic (arthoscopic) techniques have been used for achieving these same goals. Performed through a small incision, endoscopic surgery can often be performed on an outpatient basis, and recovery is often faster after the operation. It is difficult, however, to reach and tighten a tissue arthoscopically because of the difficulty in gaining access to the tissue and of controlling the degree of tightening.

A recognized property of collagen connective tissue is hydrothermal shrinkage of collagen fibers when heated. Collagen comprises fibrous crosslinked molecules. At elevated temperature, the cross links appear to be broken and the collagen fibers collapse into a more tangled configuration, with about one third of their original length. At the same time, the cross-sectional dimensions of the fibers increase greatly, but without a significant loss of strength. These characteristics of collagen connective tissue have been utilized in arthoscopic surgery to tighten the supporting structures surrounding a joint. Radio frequency radiation has been used to produce a controlled application of heat, causing the affected tissue to shrink in the direction of its fibrous structure. Commercial devices are available, for example, from Mitek Products and from ArthroCare Corporation. They have also been described in patent literature, for example, U.S. Pat. No. 5,514,130 to Baker and U.S. Pat. No. 5,681,282 to Eggers et al.

Radiant energy is usually applied arthoscopically through an electrode or another energy emitting structure carried on the end of a wand. To accommodate the diverse geometries of the various joints, wands of different configurations have been proposed. In addition to straight wands, wands having curved tips or bendable tips are known. Remotely deflectable tips for wands have been proposed. See, for example, Baker U.S. Pat. No. 5,514,130. There remain needs, however, for further development in the controlled application of heat producing energy in arthoscopic surgery.

It is an object, therefore, of our invention, to provide an arthoscopic surgical apparatus for application of heat producing energy at selected locations within the joint of the patient.

It is also an option of an object of our invention to provide an electrode bearing wand with an articulating distal tip.

A further object of our invention is to provide an electrode bearing wand with articulating tip which is self-locking in any selected articulating configuration.

Another object of our invention is to provide an electrode bearing wand with an articulating tip which can resist significant forces applied at the tip by pushing against tissue or bone of a patient's body.

Another object of our invention is to provide a wand with articulating tip which is relatively structurally rigid in any selected configuration.

SUMMARY OF THE INVENTION

We have invented a heat-producing medical apparatus having an application wand which is articulating and self-locking in a selected configuration. Preferably, the apparatus applies radio frequency radiation to contract collagen within a joint of a patient. The wand has a handle having a cylindrical chamber containing a thumb wheel apparatus. A threaded bore extends coaxially through the thumb wheel. A threaded tube received in the threaded bore translates a wire forward and backward to the distal end of the wand. The wire passes through a guide tube on the outer surface of the wand or through a lumen within the wand to the distal end of the wand. At the distal end of the wand the wire passes over a bendable section in the wand. Pushing or pulling the wire bends the distal tip through a range of angles on both sides of a neutral linear position. The distal tip remains self-locked in a selected position when the thumb screw is not turned.

DETAILED DESCRIPTION OF PREFERRED EMBODIMENTS

Figure 1:
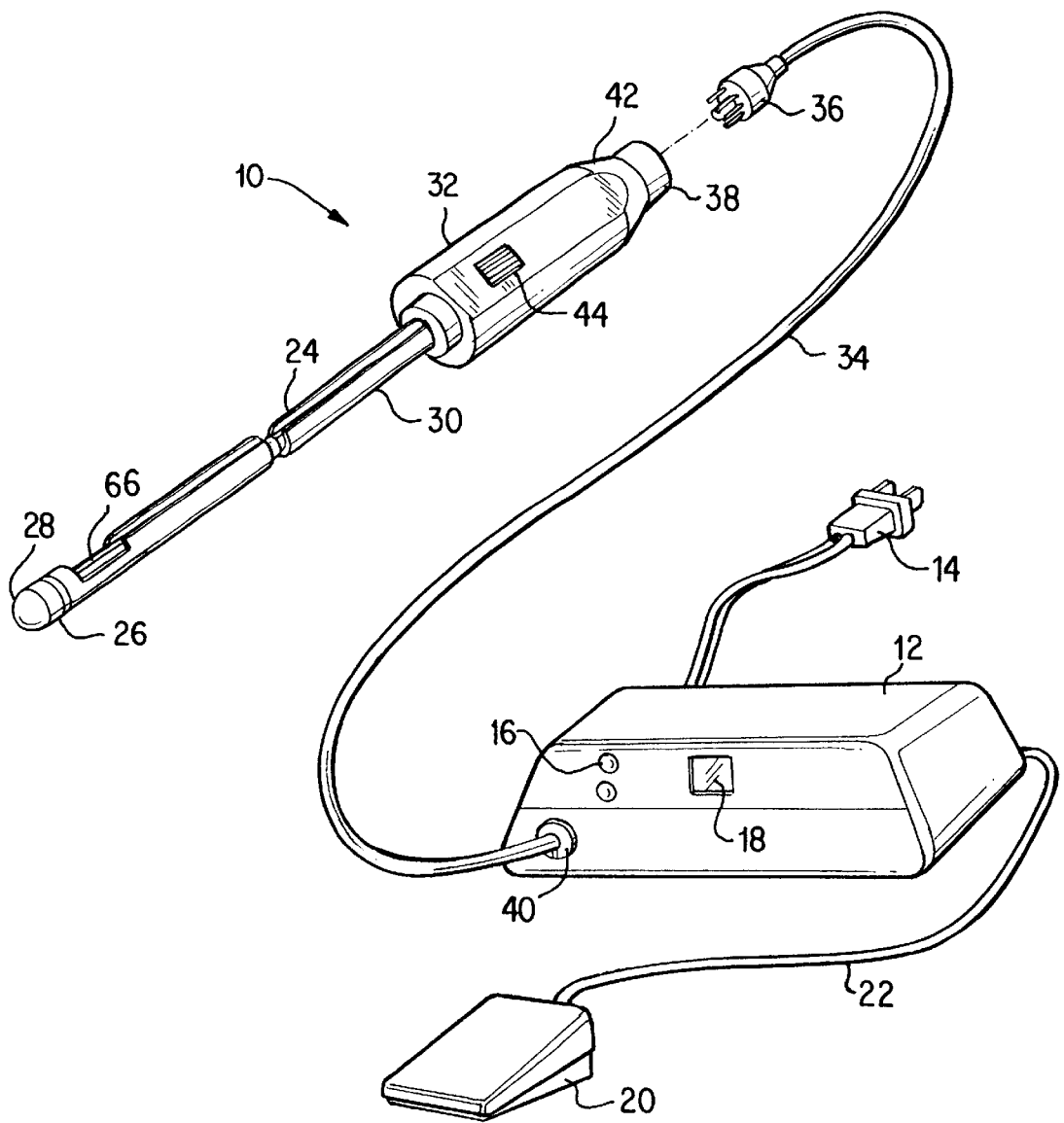
FIG. 1 is a perspective view of a radio frequency ablation apparatus in accordance with the present invention.

We will now describe a preferred embodiment of our invention with reference to the accompanying drawings. In the drawings, like numerals are used to refer to like parts throughout. FIG. 1 illustrates a perspective view of a radio frequency ablation apparatus 10 in accordance with our invention. The apparatus 10 comprises a power source for producing radio frequency (RF) electrical signals. Other heat producing radiations can also be used with our invention, for example lasers, without departing from the teachings hereof. The power source 12 is usually provided with line power through a plug 14 but may also use battery power sources. Controls 16 are used to set power levels, duration of pulses and other parameters, as is known in the art. A display 18 may be provided to assist an operator in setting the desired levels for parameters. A foot pedal control 20 or other remote control device may be provided so that an operating physician may activate the apparatus 10. Foot pedal control 20 is connected to the power source 12 by a control cable 22. Other means of remote communication, for example, infrared controls, may also be used.

A wand 24 delivers the heat producing radiation to a selected site in the body. The wand 24 has a distal end 26 bearing an electrode 28 or other energy delivery device, and a proximal end 30 connected to a handle 32. The wand 24 is electrically connected to the power source 12 through a cable 34. The cable 34 may be integrally connected to the handle 32, or, more preferably, may be connected by a male plug 36 received into a female receptacle 38 in the handle 32. Use of connectors allows the wand to be disconnected and sterilized in an autoclave or to be used as a disposable, single-use part. The cable 34 is connected to the power source 12 either directly, or through a plug 40.

Figure 2:
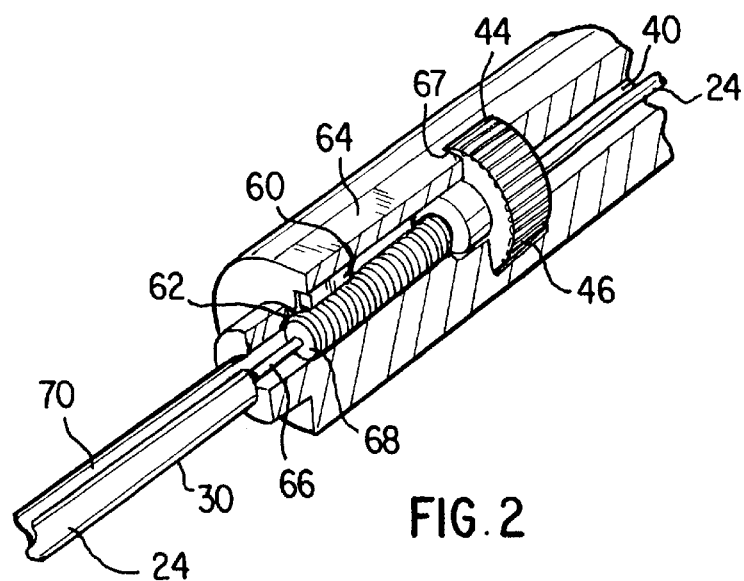
FIG. 2 is a perspective partial through section of a handle of a wand of FIG. 1 with self-locking mechanism.
Figure 3:
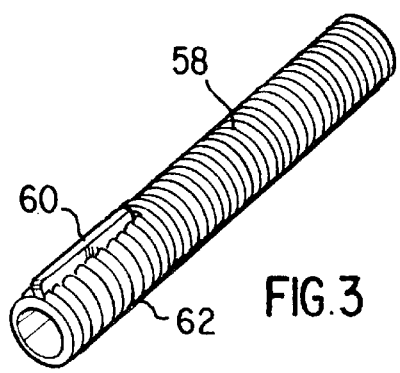
FIG. 3 is a perspective view of a threaded tube, an element from FIG. 2.
Figure 4:
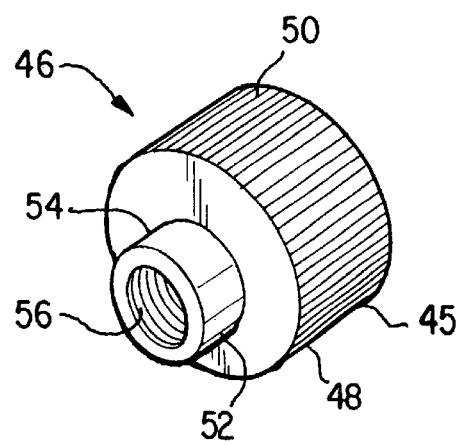
FIG. 4 is a perspective view of a thumb wheel, an element of FIG. 2.
Figure 5:
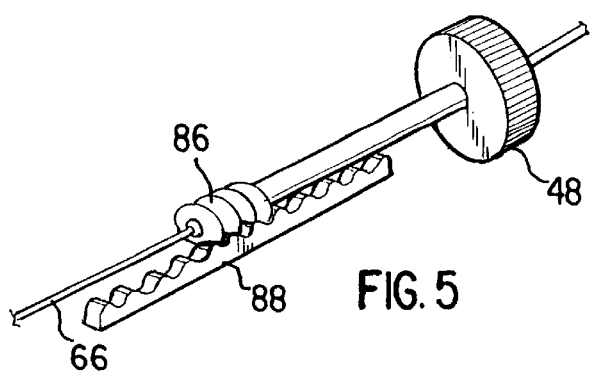
FIG. 5 is a perspective view of an alternative self-locking mechanism.
Figure 6:
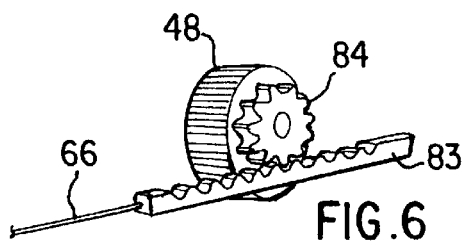
FIG. 6 is a perspective view of another alternative self-locking mechanism.
Figure 7:
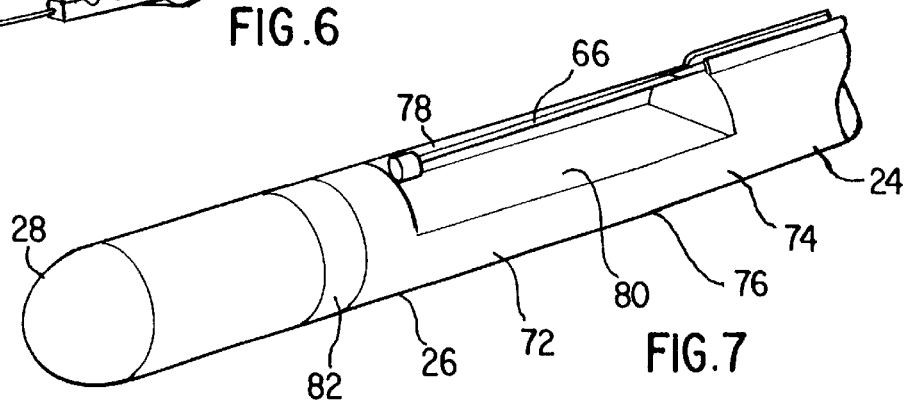
FIG. 7 is a perspective view of a distal end of a wand of FIG. 1.
Figure 8:
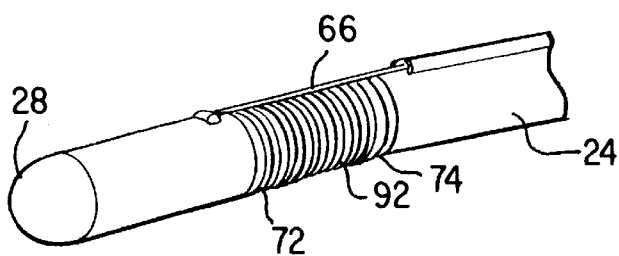
FIG. 8 is a perspective view of an alternative distal end.
Figure 9:
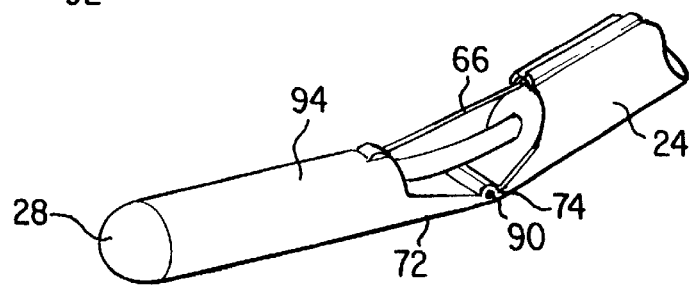
FIG. 9 is a perspective view of another alternative distal end.

Turning now to FIG. 2, the handle 32 is shown in perspective, partial through section. A handle 32 has a concentric through bore 40 through which the wand 24 passes. The wand 24 is connected electrically and mechanically to the female receptacle 38 at a proximal end 42 of the handle 32. The handle 32 has a cylindrical chamber 44 containing a thumb wheel apparatus 46. The thumb wheel apparatus 46, best seen in FIG. 4, comprises a thumb wheel 45 of generally cylindrical shape with a circumferential surface 48. Preferably ridges or other friction features 50 are provided on the circumferential surface. At least one bearing 52 may be provided, the bearing 52 comprising a cylinder having a smaller diameter than the diameter of the thumb wheel 45. The bearing 52 has a circumferential bearing surface 54, which is preferably a polished or low friction surface. A threaded through bore 56 extends coaxially through both the bearing 52 and the thumb wheel 45. A threaded tube 58 is received in the threaded bore 56. A key 60 is affixed to an outer surface 62 of the threaded tube 58. The key 60 rides in a key track 62 or groove which extends from a distal end of the handle to the chamber 44. The key 60 engaging the groove or key track 62 prevents the threaded tube 58 from turning when the thumb apparatus 46 is turned, thereby causing the threaded tube 58 to be translated forward and back within the through bore 40. A flat surface 64 on the handle, opens a window 67 into the chamber 44, exposing a portion of the circumferential surface 48 of the thumb wheel 45.

The thumb wheel apparatus 46 is self-locking, that is, when placed in a position it tends to remain in that position. The thumb wheel apparatus 46 is relatively easily manipulated by action on the thumb wheel 45, but the apparatus resists movement in response to forces applied through the threaded tube 58, such as longitudinal pushing or pulling forces. Other self-locking mechanisms will suggest themselves to those skilled in this art, as, for example, a rack 83 and pinion apparatus 84, or a worm gear 86 and mating rack 88.

Pushing or pulling forces may be produced by or transferred to the threaded tube 58 through a wire 66. The wire 66 is attached to a distal end 68 of the threaded tube 58. The wire may have any suitable cross section, for example, round, flat or ribbon-like, tubular or curved, or some other cross section. The wire 66 passes through a guide tube 70 on the outer surface of the wand 24. Alternatively, the wire 66 may pass into the wand 24 and be lead through a lumen to the distal end 26 of the wand.

At the distal end 26 of the wand 24 the wire 66 passes over a bendable section 72 in the wand. The bendable section 72 comprises a rotating or pivoting joint 74. The rotating joint 74 has a more rigid but still bendable portion 76 spaced away from the wire 66. This portion 76 may be formed by cutting away a portion 78 of the wand 24. The cut-away portion may be filled with an elastomeric segment 80.

Other forms for the joint 74 are also possible. For example, a separate component 94 may be attached to the end of the wand to act as the distal tip. A pivoting or hinged joint 90 may be provided between the wand and the distal tip. The joint may also be a coiled spring 92 or a leaf spring or other form of spring. A piece of shim-stock might be used. The joint 74 may be a component of bendable, but relatively incompressible material, such as rubber, polyurethane, or silicon based materials.

In addition to the electrode 28, an indifferent electrode 82 may also be provided at distal end of the wand, if so called "bipolar" operation is desired. Both electrodes are connected electrically to the power source 12 through conductors (not shown). As is well known in the art, a separate indifferent electrode, to be placed on the patient's body, could also be provided.

An attending physician operating the wand of our invention would manipulate the thumb wheel in a clockwise or counterclockwise direction thereby translating the threaded tube 58 longitudinally through the handle and pulling or pushing on the wire 66. Pushing or pulling the wire bends the distal tip through a range of angles on both sides of a neutral linear position. The thumb screw and threaded tube have sufficiently fine threads that the apparatus resists turning when not actively displaced by the physician. Thus, the distal tip remains self-locked in a selected position when the thumb screw is not turned. The attention of the physician is, therefore, not distracted by continually controlling the angle of the distal tip.

Preferably, the wire 66 is both relatively incompressible and relatively inextensible, thus providing a stiff displacement of the distal tip. The displaced tip therefore resists deformation except as a consequence of the action of the wire and can be forced into constricted locations within a joint.

The foregoing description of the preferred embodiment of the present invention has been provided for the purposes of illustration and description. It is not intended to be exhaustive or to limit the invention to the precise forms disclosed. Many modifications and variations will be apparent to practitioners skilled in this art. Various changes, modifications, and alterations in the teachings of the present invention may be contemplated by those skilled in the art without departing from the intended spirit and scope thereof. It is intended, therefore, that the scope of the invention be defined by the following claims and their equivalents.

What is claimed is:

1. A radio frequency ablation apparatus comprising:
   a wand having a distal end and a proximal end;
   an electrode adjacent said distal end of said wand;
   a handle connected to said proximal end of said wand, and having a chamber inside said handle;
   an electrical connector mounted on said handle and electrically connected to said electrode;
   a wheel mounted in said handle, said wheel having a driving portion thereon, said wheel being contained within said chamber, and
   a window opening into said chamber through said handle, said wheel being partially exposed through said window;
   a threaded shaft connected to said driving portion and movable longitudinally thereby; and
   a wire coupling said threaded shaft and said distal end of said wand.

2. The radio frequency ablation apparatus of claim 1 further comprising
   a tube coupled a long an outer surface of said wand, said tube slidingly housing said wire.

3. The radio frequency ablation apparatus of claim 2 further comprising
   a bendable section of said wand proximal to said distal end of said wand.

4. The radio frequency ablation apparatus of claim 3 wherein said tube extends immediately proximally of said bendable section and said wire extends distally of said bendable section.

5. The radio frequency ablation apparatus of claim 4 wherein said bendable section consists of a reduced part of said wand adjacent said wire.

6. The radio frequency ablation apparatus of claim 4 wherein said bendable section consists of an elastomeric segment.

7. The radio frequency ablation apparatus of claim 4 wherein said bendable section consists of a rotating joint.

8. The radio frequency ablation apparatus of claim 4 wherein said bendable section consists of a coiled spring.

9. The radio frequency ablation apparatus of claim 1 further comprising
   a bearing coupled to said wheel, and
   a bearing surface within said handle, said bearing surface supporting said bearing.

10. The radio frequency ablation apparatus of claim 9 wherein said bearing comprises a cylinder and said bearing surface comprises a cylindrical chamber, said cylinder being slidingly received in said cylindrical chamber.

11. The radio frequency ablation apparatus of claim 1 further comprising
    a pin extending from said threaded shaft and slidingly received in a slot in said handle.

12. The radio frequency ablation apparatus of claim 1 further comprising a pivoting attachment connecting said wire to said distal end of said wand.

13. The radio frequency ablation apparatus of claim 1 wherein said driving portion comprises a threaded bore and said shaft is a threaded shaft is received in said bore.

14. The radio frequency ablation apparatus of claim 1 wherein said driving portion comprises a worm gear and said shaft is a threaded shaft coupled to said gear.

15. The radio frequency ablation apparatus of claim 1 wherein said driving portion comprises a pinion gear and said shaft is a rack coupled to said gear.

16. A medical catheter comprising:
    a wand having a distal end and a proximal end;
    a handle connected to said proximal end of said wand and having a chamber within said handle;
    a wheel mounted within said chamber in said handle, said wheel having a driving portion thereon, and said handle having a window opening into said chamber through said handle, said wheel being partially exposed through said window; and
    a stylet, said stylet having
       a shaft connected to said driving portion; and
       a wire coupling said shaft and said distal end of said wand.

17. The medical catheter of claim 16 further comprising
    a tube coupled along an outer surface of said wand, said tube slidingly housing said wire.

18. The medical catheter of claim 17 further comprising
    a bendable section of said wand proximal to said distal end of said wand.

19. The medical catheter of claim 18 wherein said tube extends immediately proximally of said bendable section and said wire extends distally of said bendable section.

20. The medical catheter of claim 19 wherein said bendable section consists of a reduced part of said wand adjacent said wire.

21. The medical catheter of claim 19 wherein said bendable section consists of an elastomeric segment.

22. The medical catheter of claim 19 wherein said bendable section consists of a rotating joint.

23. The medical catheter of claim 19 wherein said bendable section consists of a coiled spring.

24. The medical catheter of claim 16 further comprising
    a bearing coupled to said wheel, and
    a bearing surface within said handle, said bearing surface supporting said bearing.

25. The medical catheter of claim 24 wherein said bearing comprises a cylinder and said bearing surface comprises a cylindrical chamber, said cylinder being slidingly received in said cylindrical chamber.

26. The medical catheter of claim 16 further comprising
    a pin extending from said stylet and slidingly received in a slot in said handle.

27. The medical catheter of claim 16 further comprising a pivoting attachment connecting said wire to said distal end of said wand.

28. The medical catheter of claim 16 wherein said driving portion comprises a threaded bore and said shaft is a threaded shaft is received in said bore.

29. The medical catheter of claim 16 wherein said driving portion comprises a worm gear and said shaft is a threaded shaft coupled to said gear.

30. The medical catheter of claim 16 wherein said driving portion comprises a pinion gear and said shaft is a rack coupled to said gear.

31. A radio frequency ablation apparatus comprising:
- a radio frequency power source;
- a wand having a distal end and a proximal end;
- an electrode adjacent said distal end of said wand;
- a handle connected to said proximal end of said wand, and having a chamber in said handle;
- an electrical conductor electrically connecting said radio frequency power source to said electrode;
- a wheel mounted in said handle, said wheel having a driving portion thereon, said wheel being contained within said chamber in said handle, and
- a window opening into said chamber through said handle, said wheel being partially exposed through said window; and
- a stylet, said stylet having
  - a shaft connected to said driving portion; and
  - a wire coupling said shaft and said distal end of said wand.

32. The radio frequency ablation apparatus of claim 31 further comprising a tube coupled along an outer surface of said wand, said tube slidingly housing said wire.

33. The radio frequency ablation apparatus of claim 32 further comprising a bendable section of said wand proximal to said distal end of said wand.

34. The radio frequency ablation apparatus of claim 33 wherein said tube extends immediately proximally of said bendable section and said wire extends distally of said bendable section.

35. The radio frequency ablation apparatus of claim 34 wherein said bendable section consists of a reduced part of said wand adjacent said wire.

36. The radio frequency ablation apparatus of claim 34 wherein said bendable section consists of an elastomeric segment.

37. The radio frequency ablation apparatus of claim 34 wherein said bendable section consists of a rotating joint.

38. The radio frequency ablation apparatus of claim 34 wherein said bendable section consists of a coiled spring.

39. The radio frequency ablation apparatus of claim 31 further comprising
- a bearing coupled to said wheel, and
- a bearing surface within said handle, said bearing surface supporting said bearing.

40. The radio frequency ablation apparatus of claim 39 wherein said bearing comprises a cylinder and said bearing surface comprises a cylindrical chamber, said cylinder being slidingly received in said cylindrical chamber.

41. The radio frequency ablation apparatus of claim 31 further comprising
- a pin extending from said stylet and slidingly received in a slot in said handle.

42. The radio frequency ablation apparatus of claim 31 further comprising a pivoting attachment connecting said wire to said distal end of said wand.

43. The radio frequency ablation apparatus of claim 31 wherein said driving portion comprises a threaded bore and said shaft is a threaded shaft received in said bore.

44. The radio frequency ablation apparatus of claim 31 wherein said driving portion comprises a worm gear and said shaft is a threaded shaft coupled to said gear.

45. The radio frequency ablation apparatus of claim 31 wherein said driving portion comprises a pinion gear and said shaft is a rack coupled to said gear.

* * * * *